United States Patent [19]
Wihlborg

[11] Patent Number: 5,445,794
[45] Date of Patent: Aug. 29, 1995

[54] LUMINESCENCE MEASURING SYSTEM AND LUMINOMETER DEVICE

[75] Inventor: Nils Wihlborg, Helsingborg, Sweden

[73] Assignee: Perstorp Analytical AB, Helsingborg, Sweden

[21] Appl. No.: 232,049

[22] PCT Filed: Oct. 29, 1992

[86] PCT No.: PCT/SE92/00749

§ 371 Date: Apr. 26, 1994

§ 102(e) Date: Apr. 26, 1994

[87] PCT Pub. No.: WO93/09420

PCT Pub. Date: May 13, 1993

[30] Foreign Application Priority Data

Oct. 29, 1991 [SE] Sweden ............... 9103150-0

[51] Int. Cl.$^6$ ........................................ G01N 21/13
[52] U.S. Cl. ........................ 422/63; 422/52; 422/65; 422/67; 422/82.05; 422/103; 422/104; 436/43; 436/47; 436/48; 436/172; 436/805
[58] Field of Search .............. 422/52, 50, 63, 65, 422/67, 68.1, 82.05, 104, 103; 436/43, 45, 48, 172, 805, 47; 356/640, 441, 442

[56] References Cited

U.S. PATENT DOCUMENTS

| | | | |
|---|---|---|---|
| 4,366,118 | 12/1982 | Bunce et al. | 422/57 |
| 4,863,690 | 9/1989 | Berthold et al. | 422/52 |
| 5,316,726 | 5/1994 | Babson et al. | 422/65 |

FOREIGN PATENT DOCUMENTS 0226374 6/1987 European Pat. Off. .
223095 3/1990 United Kingdom .

OTHER PUBLICATIONS

Rawlins and Peacock, Design principles for a modern luminometer, International Laboratory, vol. 12 (5), pp. 48–56, 1982.

Primary Examiner—James C. Housel
Assistant Examiner—Long V. Le
Attorney, Agent, or Firm—Burns, Doane, Swecker & Mathis

[57] ABSTRACT

A luminescence measuring system comprises an apparatus for supplying samples located in separate test tubes. In the measuring chamber of a luminometer, the samples are in turn presented to a light detector, such as photomultiplier. Two mutually displaceable components, which are cup-shaped and fit into one another with the cup bottoms facing outwards, define the measuring chamber. The component shells are provided with holes which can be aligned by relative displacement of the components so as to admit the test tube into the luminometer and the measuring chamber and subsequently to discharge it therefrom under the action of gravity. The test tubes are conveyed to the luminometer by a sleeve-chain conveyor having a bottom with a through hole.

16 Claims, 4 Drawing Sheets

LUMINESCENCE MEASURING SYSTEM AND LUMINOMETER DEVICE

The present invention relates to a luminescence measuring system and a luminometer device, i.e. a device which is designed for making bioluminescence and chemiluminescence measurements and in which test tubes with the substances to be analysed by luminescence are conveyed, in a series of test-tube holders, past a measuring station having a light detector, such as a photomultiplier.

EP-A-0 226 374 and U.S. Pat. No. 4,863,690, for instance, disclose luminescence measuring systems. The former publication describes a complex rotary device for removing the test tubes from the holders one after the other and introducing them into a measuring chamber, which itself is of complex design. The latter publication describes a measuring system having special holders for the test tubes.

The objects of the invention are to provide a luminescence measuring system and a luminometer device which is simple, does not require any special holders for the test tubes, and is reliably lightproof during the measurements.

According to the invention, these objects are achieved by a luminescence measuring system and a luminometer device as defined in the appended claims.

The invention will be described in more detail below with reference to the accompanying drawings, in which FIG. 1 is a perspective view of the inside of a movable component of the device;

Figure 1:
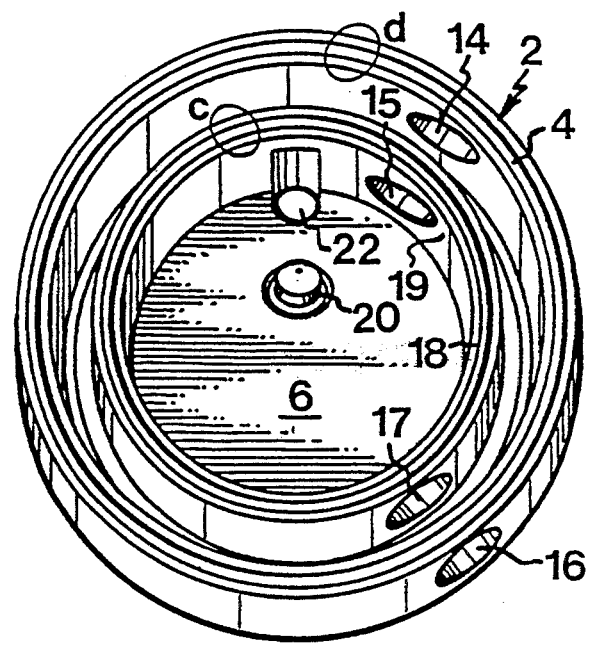
Figure 2:
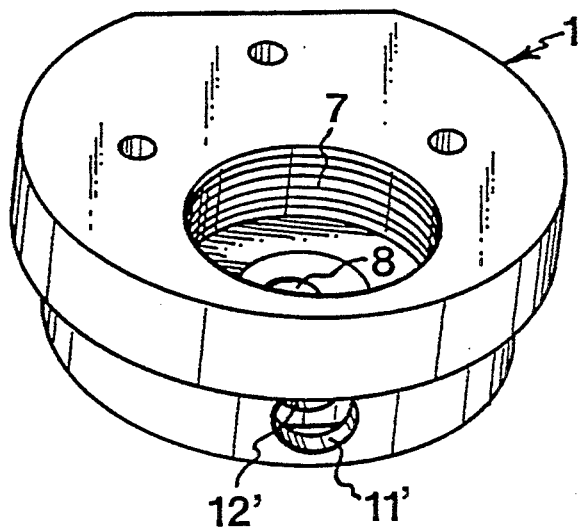
FIG. 2 is a perspective view of the outside of a fixed component.
Figure 3:
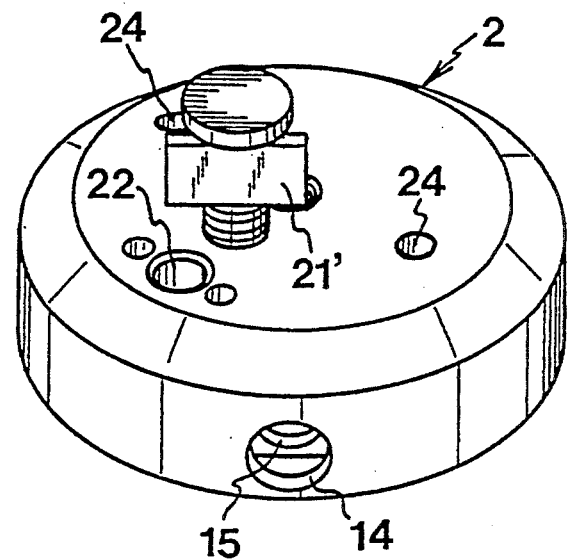
FIG. 3 is a perspective view of the outside of the movable component.
Figure 4:
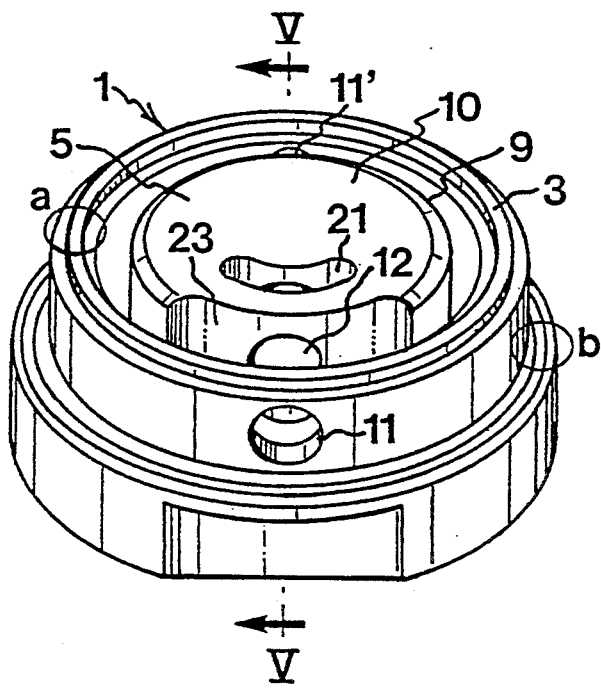
FIG. 4 is a perspective view of the inside of the fixed component.
Figure 5:
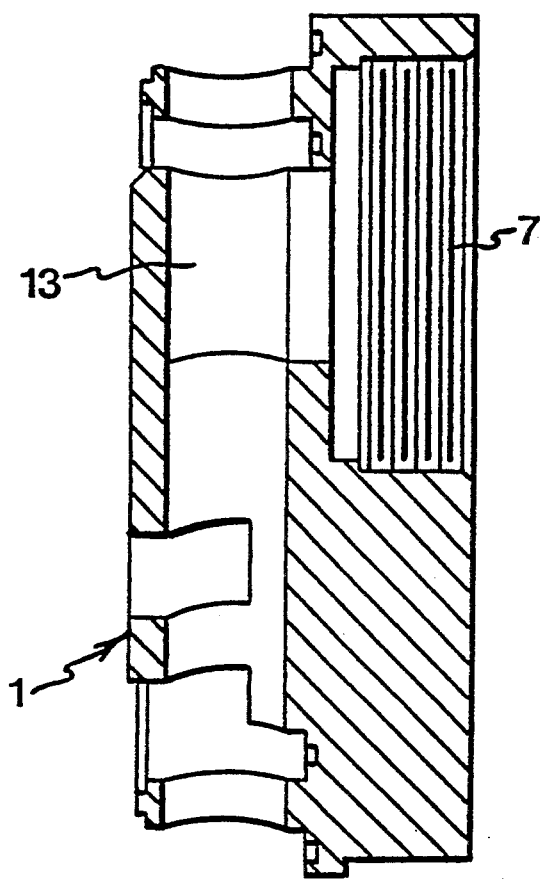
FIG. 5 is a sectional view of the fixed component taken along the line V—V in FIG. 4.

The luminometer comprises a cup-shaped component 1 which is fixedly mounted on a frame, and a cup-shaped component 2 which is rotatable round the fixed component 1 about a common axis and which forms a lid for the fixed component 1 when an annular flange or shell wall 3 of the fixed component has been fitted into an annular groove 4 in the movable component 2. The annular flange 3 encloses a measuring chamber 5 in the fixed component 1. This chamber can be accommodated in a space 6 in the movable component 2. The measuring chamber 5 is fitted in the space 6 with sliding fit, as is the flange 3 in the annular groove 4. The components are made in one piece.

Figure 6:
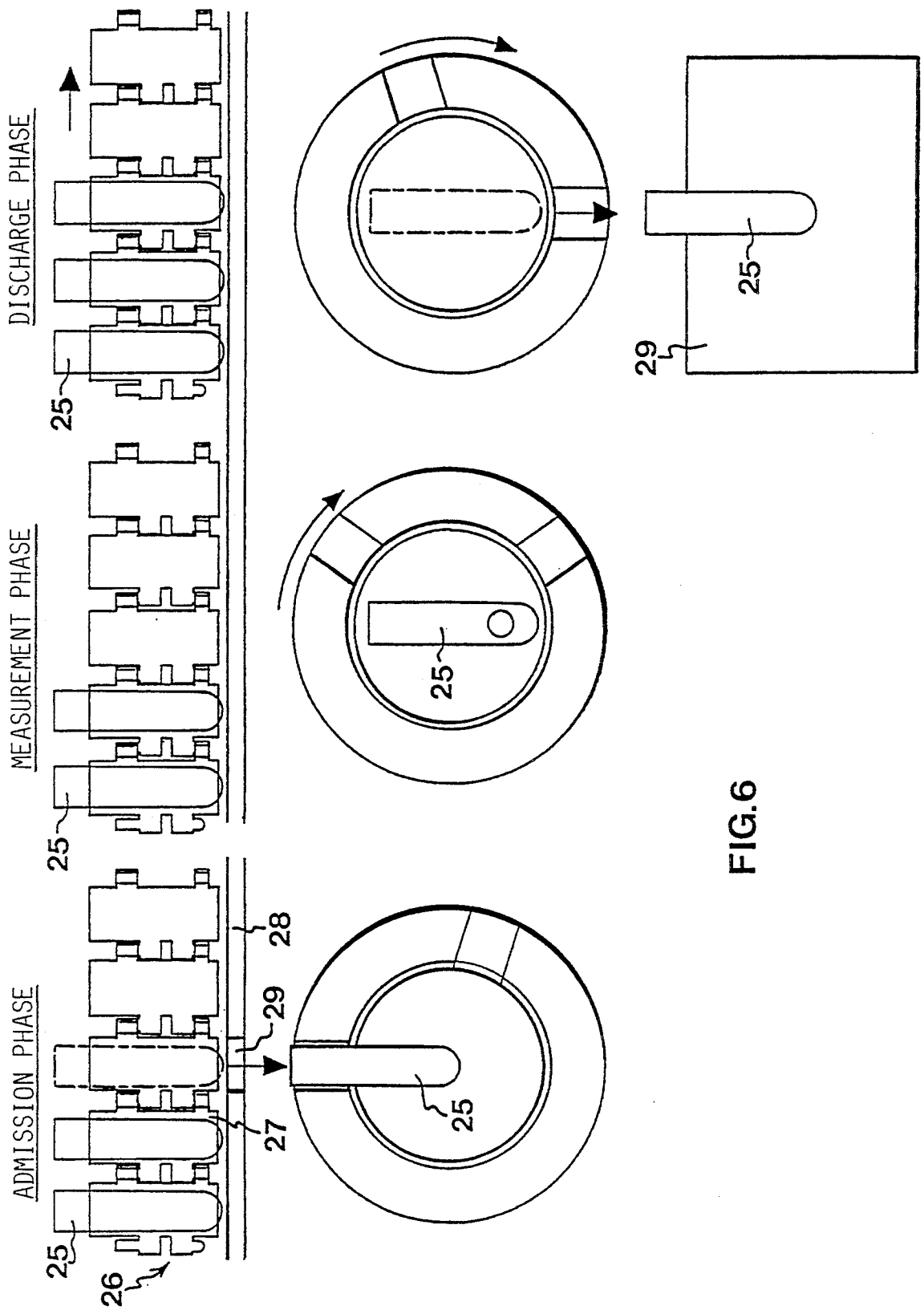
FIG. 6 schematically illustrates the operation of the inventive device in association with a chain conveyor for test tubes, forming a luminescence measuring system.

At the outside, the component 1 has a threaded hole 7 in which the head of a photomultiplier (not shown) can be screwed. The bottom wall of the hole 7 defines a smaller circular hole 8 having a diameter Just about equal to the diameter of the test tube (such as 25 in FIG. 6) whose content is to be analysed by luminescence measurement. The hole 8 opens in the measuring chamber 5, which is defined by a closed peripheral wall 9 and a top 10. The flange 3 and the peripheral Wall 9 are provided with through holes 11, 12, 11', 12', which all are located on a common diameter of the component 1, the diametral line passing through The centre of the hole 8. The diameter of the through holes 11, 12, 11', 12'; slightly exceeds that of the test tubes. A dome-shaped recess 13 extends from the hole 12 to the hole 12' so as to guide the lower sample-containing part of a test tube to a position opposite to the hole 8. The distance between the holes 12 and 12' equals the length of the test tube.

The component 2 is also provided with holes 14, 15, 16, 17 in its outer shell wall and in the flange or inner shell wall 18 which, together with the outer shell wall, defines the annular groove 4 and which defines the space 6 for the measuring chamber 5. The holes 14, 15 are aligned along a common diameter, as are the holes 16, 17. However, the axes of the pairs of holes 14, 15 and 16, 17 form an angle of about 70° with one another.

It will now be appreciated that, when the components 1 and 2 engage one another, the holes 14, 15 and 16, 17 can be brought into alignment with the holes 11, 11' and 12, 12', respectively, by rotating the movable component 2, so as to allow test tubes to enter as well as leave the measuring chamber 5. An intermediate position in which light is screened off provides a measuring position. It is also understood that the test tube can only be admitted or discharged under the action of gravity, if, as intended, the holes 11, 12, 11', 12' of the fixed component 1 contain the vertical.

Enhanced lightproofness in luminescence measurements can be achieved by ribs and contersunk portions on/in mating parts of the components 1 and 2 (see the encircled parts a, b, c, d).

After admission, the test tube will rest in the measuring chamber 5 with its lower sample-containing part located opposite to the hole 8 by abutting against the inner surface 19 of the flange 18.

A spring-loaded cam 20 is arranged in the movable component 2 to follow a groove 21 in the top 10. The cam 20 is adapted to turn on an electric switch 21' when it is moved apart, against the spring load, by a test tube in the measuring chamber during the rotation of the movable component 2. The switch 21' is adapted to actuate a pump for supplying a reagent to the test tube. The reagent is supplied through a bent injection needle and a hose (not shown). The injection needle is introduced from outside in a lightproof manner through a hole 22 in the component 2 and follows the movement thereof in a recess 23 in the peripheral wall 9 of the measuring chamber.

The movable component 2 is rotated by an electric step motor (not shown), whose shaft engages dead holes 24 in the outside of the movable component and which rotates the movable component 2 between the measuring position and, alternatingly, the admission and discharge positions.

The test tubes 25 are conveyed in a chain after one another along a path (FIG. 6) comprising a motor-driven conveyor 26 with chain links consisting of sleeves 27, each containing test tubes with material to be analysed in the measuring chamber by luminescence.

The test tubes 25 are fitted in the sleeves 27 with sliding fit. When conveyed towards the luminometer, the test tubes are supported by their base portions on a support structure or bottom 28 having a hole 29 which is located opposite to the holes 11, 12, 11', 12' of the fixed component 1, and adapted to let through the test tubes.

The measuring procedure is controlled by a computer in the following manner.

When a sleeve 27 with a test tube 25 reaches, along its conveying path, the hole 29 straight above the site of the luminometer, the rotatable component 2 is set in the measuring position described above. The computer stops the conveyor 26, and the test tube 25 descends into the hole 29 so as to abut against the outer shell of the component 2. Normally, i.e. when the preceding test tube has been discharged from the measuring chamber, the motor then receives a signal from the computer to rotate the movable component 2 in a direction to bring the holes 11, 12 (11', 12') and the holes 14, 15 into vertical alignment straight below the hole 29, and the test tube 25 drops into the measuring chamber 5.

The computer then transmits a signal to the motor to rotate the movable component to the luminescence-sensing measuring position, in which the presence of the test tube is sensed by the elements 20, 21 so as to activate the reagent pump which injects the reagent into the test tube through the injection needle. The dwell time, determined by the computer, of the sample in the measuring chamber is about 10 s in the case of bioluminescence measurement with LUMIT ® for determination of ATP. Then, the computer signals to the motor to rotate the movable component in a direction to bring the holes 11', 12' (11, 12) into alignment with the holes 16, 17, whereby the test tube can be discharged, under the action of gravity, from the luminometer to a collection site 29, which may be a waste container or, if the sample is to be further analysed, a sleeve in another test-tube conveyor.

In the event a test tube, for some reason or other, is left in the measuring chamber 5 in engagement with the cam 20 in the measuring chamber 5 when a new sample is to be analysed, the computer is adapted to actuate the motor to once again rotate the movable component to the discharging position, without any preceding actuation of the reagent pump. Further, if no new test tube is admitted into the measuring chamber 5 after a preceding discharge, the computer is adapted to actuate the motor to rotate the movable component once again to the admitting position without any preceding injection of reagent.

It is understood that the inventive idea of admitting and discharging samples under the action of gravity can be implemented also in other ways. Thus, the admitting and discharging positions are not necessarily reached by rotation. Alternatively, use is made of square components 1 and 2, in which case the component 2 is displaced in a translational fashion on the fixed component 1.

I claim:

1. A luminescence measuring system comprising:
   a conveyor for delivering containers of samples for luminescence measurements, including a translationally drivable chain of vertically disposed tubular sleeves, each sleeve for carrying a container, and a fixed bottom provided with a hole, said chain of sleeves being displaceable relative to the bottom above the hole to align the tubular sleeves with the hole so that a container exits an aligned tubular sleeve through said hole under the action of gravity; and
   a luminometer disposed below the bottom of the conveyor to receive the containers from the conveyor through the hole, the luminometer comprising two cup-shaped components, each having at least a peripheral shell and a base side, the components being relatively displaceable and disposed so that the peripheral shells mutually engage, an interior measuring chamber in one of the components being enclosed by the shells and outer facing base sides;
   wherein each shell has an admission hole and an exit hole communicating with the measuring chamber, the components having a first relative position wherein the admission holes are positioned vertically above the measuring chamber and aligned with the hole in the bottom of the conveyor, and a second relative position wherein the exit holes are aligned in a position vertically below the measuring chamber; and
   wherein alignment of the admission holes and the hole in the bottom allows a container to move from the conveyor into the measuring chamber by action of gravity and alignment of the exit holes allows the container to exit the measuring chamber by action of gravity.

2. A luminescence measuring system as set forth in claim 1, wherein said components are relatively displaceable by rotation.

3. A luminescence measuring system as set forth in claim 1, wherein the two cup-shaped components each have an inner shell and an outer shell.

4. A luminescence measuring system as set forth in claim 3, wherein a first cup-shaped component further comprises a top attached to the inner shell and the top, inner shell and the base define the measuring chamber.

5. A luminescence measuring system as set forth in claim 4, wherein said top includes a guide slot and a second component further comprises a spring-loaded cam projecting from the base side through the slot into the measuring chamber for sensing the presence and the absence of a container in the measuring chamber.

6. A luminescence measuring system as set forth in claim 2, wherein the two cup-shaped components each have an inner shell and an outer shell.

7. A luminescence measuring system as set forth in claim 6, wherein a first cup-shaped component further comprises a top attached to the inner shell and the top, inner shell and base of the first component define the measuring chamber (5).

8. A luminescence measuring system as set forth in claim 7, wherein said top includes a guide slot and a second component further comprises a spring-loaded cam projecting from the base of the second component through the slot into the measuring chamber for sensing the presence and the absence of a container in the measuring chamber.

9. A luminometer device comprising:
   a luminometer comprising two cup-shaped components, each having at least a shell and a base side, the components being relatively displaceable and disposed so that the shells engage so that an interior measuring chamber in one of the components is enclosed by the shells and by the base sides;
   wherein each shell has an admission hole and an exit hole communicating with the measuring chamber, the components having a first relative position wherein the admission holes are aligned vertically above the measuring chamber, and a second relative position wherein the exit holes are aligned in a position vertically below the measuring chamber; and
   wherein alignment of the admission holes allows a container to move from a position above the admission holes into the measuring chamber by action of gravity and alignment of the exit holes allows the container to exit the measuring chamber by action of gravity, 10. A luminometer device as set forth in claim 9, wherein said components (1, 2) are relatively displaceable by rotation.

11. A luminometer device as set forth in claim 9, wherein the two cup-shaped components each have an inner shell and an outer shell.

12. A luminometer device as set forth in claim 11, wherein a first cup-shaped component further comprises a top attached to the inner shell and the inner, top and base define the measuring chamber.

13. A luminometer device as set forth in claim 12, wherein said top includes a guide slot and a second component further comprises a spring-loaded cam projecting from the base of the second component through the slot into the measuring chamber for sensing the presence and the absence of a container in the measuring chamber.

14. A luminometer device as set forth in claim 10, wherein the two cup-shaped components each have an inner shell and an outer shell.

15. A luminometer device as set forth in claim 14, wherein a first cup-shaped component further comprises a top attached to the inner shell and the top, inner shell and base of the first component define the measuring chamber.

16. A luminometer device as set forth in claim 15, wherein said top includes a guide slot and a second component further comprises a spring-loaded cam projecting from the base of the second component through the slot into the measuring chamber for sensing the presence and the absence of a test tube in the measuring chamber.

* * * * *